US006183646B1

(12) United States Patent
Williams et al.

(10) Patent No.: US 6,183,646 B1
(45) Date of Patent: Feb. 6, 2001

(54) BIOFOULING REDUCTION

(75) Inventors: Edward Emyr Williams, Dore Sheffield; Peter William Nickson, Newbury; Brent Roland Knox-Holmes, Sheffield; Robert Wainwright, Northants, all of (GB)

(73) Assignee: Baker Hughes Incorporated, Houston, TX (US)

(*) Notice: Under 35 U.S.C. 154(b), the term of this patent shall be extended for 0 days.

(21) Appl. No.: 09/000,079

(22) PCT Filed: Jul. 15, 1996

(86) PCT No.: PCT/IB96/01015

§ 371 Date: Dec. 14, 1998

§ 102(e) Date: Dec. 14, 1998

(87) PCT Pub. No.: WO97/03926

PCT Pub. Date: Feb. 6, 1997

(30) Foreign Application Priority Data

Jul. 19, 1995 (GB) .................................... 9514830

(51) Int. Cl.⁷ .................................................. B01D 61/10
(52) U.S. Cl. ................... 210/636; 210/199; 210/321.69; 210/652; 210/752; 210/758; 422/28; 422/37
(58) Field of Search ................. 210/143, 198.1, 210/199, 206, 241, 258, 259, 321.6, 321.69, 636, 650, 652, 752, 754, 756, 760, 764, 806, 192, 243, 758; 422/28, 29, 31, 37

(56) References Cited

U.S. PATENT DOCUMENTS

| 3,241,512 | 3/1966 | Green . | |
|---|---|---|---|
| 4,177,143 | 12/1979 | Myers . | |
| 4,216,185 | 8/1980 | Hopkins | 422/28 |
| 4,278,548 | * 7/1981 | Bettinger et al. | 210/639 |
| 4,311,598 | 1/1982 | Verachtert | 210/764 |
| 4,724,079 | * 2/1988 | Sale et al. | 210/652 |
| 4,804,478 | 2/1989 | Tamir | 210/752 |
| 4,869,016 | * 9/1989 | Diprose et al. | 210/652 |
| 4,988,444 | * 1/1991 | Applegate et al. | 210/636 |
| 5,008,075 | 4/1991 | Rufolo . | |
| 5,040,487 | 8/1991 | Bollyky et al. . | |
| 5,133,876 | 7/1992 | Tharp | 210/758 |
| 5,217,626 | * 6/1993 | Yahya et al. | 210/764 |
| 5,252,300 | 10/1993 | Hinchliffe | 210/760 |
| 5,292,405 | 3/1994 | Wicks . | |
| 5,366,622 | 11/1994 | Geyer . | |
| 5,547,584 | * 8/1996 | Capehart | 210/652 |

FOREIGN PATENT DOCUMENTS

| 141330 | 9/1929 | (CH) . |
| 149723 | 12/1931 | (CH) . |
| 593 363 | 2/1934 | (DE) . |

(List continued on next page.)

*Primary Examiner*—Joseph W. Drodge
(74) *Attorney, Agent, or Firm*—Trask Britt

(57) ABSTRACT

The invention relates to the reduction and prevention of biofouling in facilities utilizing water, e.g. sea water, carrying biological organisms, without causing corrosion, chemical reaction or other detrimental action from the additive or environmental discharge problems. Such operations include, for example, desalination plants, power plants, oilfield water injection facilities and shipboard or ocean platform fire water systems. For example, in the desalination plant of FIG. 1, the biofouling reduction method and apparatus for this invention have a source of oxidizing agent such as chlorine ions or ozone, a source of copper ions and a dosing chamber for delivery of relatively low dosage levels of oxidizing agents and at appropriate times copper ions to form a treatment additive. Flow connectors connect the dosing chamber to various points along the piping in the desalination plant. A controller controls the operation of the dosing chamber and valves along the flow connectors to operate in a sequential target dosing mode to deliver treatment additive of predetermined composition to selected points along the piping at predetermined times and in predetermined concentrations.

23 Claims, 4 Drawing Sheets

FOREIGN PATENT DOCUMENTS

| | | |
|---|---|---|
| 3344275 A1 | 6/1985 | (DE) . |
| 0 024 875 A2 | 3/1981 | (EP) . |
| 0 077 208 A1 | 4/1983 | (EP) . |
| 0 302 501 A1 | 2/1989 | (EP) . |
| 0 397 184 A1 | 5/1990 | (EP) . |
| 0 549 413 A1 | 12/1992 | (EP) . |
| 876741 | 9/1961 | (GB) . |
| 1158545 | 7/1969 | (GB) . |
| 2 207 912 | 2/1989 | (GB) . |
| 2 207 911 | 8/1989 | (GB) . |
| 53-106388 | 9/1978 | (JP) . |
| 07016581 | 1/1995 | (JP) . |

* cited by examiner

BIOFOULING REDUCTION

BACKGROUND OF THE INVENTION

1. Field of the Invention

This invention relates to biofouling reduction, and, more particularly, to the reduction and prevention of biofouling in facilities utilizing water, such as sea water, carrying biological organisms.

2. State of the Art

Control of fouling in facilities utilizing process water has been a long-standing problem. Macroorganisms, such as species of mussels, including zebra mussels, found in sea water and fresh water sources, such as the Great Lakes, have become notorious sources of biofouling. With their ability to grow profusely and in great concentration, mussels, including zebra mussels, have been known to completely block and close large diameter water inlet pipes for the cooling systems of major seaside and lakeside power plants. While less notorious, microorganism fouling can be just as troubling. Such fouling can reduce heat transfer through the piping and reduce the flow of water through the piping of heat exchangers, thereby decreasing their ability to discharge heat into the water. In addition, such fouling can adversely change the permeability of filters (and, more particularly, the permeability of the filtration media contained within the filters). In addition, macroorganisms and microorganisms within piping systems generate chemical waste products that induce and promote chemical corrosion within the systems. This phenomenon, commonly known as microbially induced corrosion, attacks the structural integrity of piping systems.

Various techniques have been proposed to prevent, or at least reduce biofouling, but all have had their limitations. Among the early attempts was the use of heavy dosages of chlorine ions as a biocide to kill the organisms. While this approach gave the desirable result of sanitizing the water, it also produced undesirable excess hypochlorous acid which itself attacked the structural integrity of the piping system. More recently, environmental concerns have been raised about the high doses of chlorine and, in particular, the discharge of residual (or unreacted) chlorine and reaction products, such as trihalomethanes, from the piping system back into the ecology.

Similarly, high doses of copper ions have been proposed as a biocide. As with chlorine, the discharge of high levels of residual copper ions back into the ecosystem presents a significant environmental concern. In addition, it has been found that at least certain microorganisms have responded to copper ion treatment by developing a degree of resistance to this biocide. Copper ion alone is regarded as effective only against macrofouling. Moreover, typically, electrolytic cells utilizing copper electrodes are used to generate the copper ions, and these electrodes experience a high rate of sacrificial loss in generating the needed dosage level of ions.

A more recent and more promising approach was jointly developed by certain of the inventors of the instant invention in their U.S. Pat. No. 4,869,019, incorporated herewith by reference. This patent describes the synergistic effect of low dosage levels of chlorine ions used in conjunction with low dosage levels of copper ions to form a treatment additive sufficient to temporarily stress or disorient (but not "necessarily" kill) both macroorganisms and microorganisms so that they pass through the piping system of a facility without attaching themselves to the system. Being of low dosage, the chlorine and copper ions generated by this technique represent significantly less environmental concern than the previous techniques. As successful as this combined ion treatment approach may have been, it still suffered limitations as applied to large facilities. Combined ion treatment is effective for only a relatively short time duration (such as, for example, thirty (30) minutes). Thus, if combined ion treatment is used only at the water inlet to the piping system of a large facility, the treatment is effective for only part of the travel of the organisms through the piping system. Fouling can then occur in the downstream part of the piping system for which treatment effectiveness has been lost. Conversely, use of combined ion treatment at numerous points along the piping system requires a corresponding number of sources of ion generation, such as electrolytic cells for generating the treatment ions, with resultant increased capital costs and operating expenses, and can result in an environmentally unacceptable buildup of certain of the ions at discharge.

Among the facilities not adequately treated for biofouling by these prior art techniques are desalinization plants. These plants use reverse osmosis semipermeable membranes to remove inorganic ions, such as salt, from sea water or fresh water brines. However, biological organisms carried along with the sea water and brines tend to grow on the semipermeable membranes of these cells, causing them to lose permeability and thus to lose salt removal efficiency. This lost efficiency at times has exceeded 50%, thereby reducing fresh water production or requiring additional production capacity. Typically, biofouling treatment of such facilities takes the form of adding high dosage levels of chlorine ions at the inlet to the piping system. While this may sanitize the water of organisms, the high dosage level of chlorine itself can, in some instances, chemically react with the media and adversely affect its permeability. Moreover, the generation of high dosage levels of chlorine is expensive in terms of capital equipment required and operating expenses, and the disposal of such levels of chlorine can present environmental problems.

Another difficult biofouling problem is presented by marine fire water systems. These systems are found on board ships, oilfield offshore rigs and production and storage facilities, and take the form of a ring main with fire extinguishing sprinkler and deluge system utilizing sea water constantly charged under pressure in the system. Over time, the biological organisms in the water grow, stimulating the production of corrosion product and blocking the piping system, thereby preventing water discharge when needed. Prior art systems called for a constant, relatively small volume discharge of sea water from the system and the delivery of high dosage levels of chlorine at the water inlet to the system. However, chlorine at these levels causes and enhances corrosion of the piping system and presents environmental problems at discharge. Other approaches for solving this problem include the use of high alloy brass, such as Admiralty Brass, as the material of construction of the piping system. Such materials leach copper ions to retard biological growth, but are expensive and difficult to install.

Further biofouling problems arise with facilities having numerous points requiring biofouling treatment, such as, for example, power plants having a bank of heat exchangers in parallel flow arrangement, and oilfield water injection apparatus for injecting treated water into a water bearing formation of a hydrocarbon reservoir having a number of filter units in series or parallel flow arrangement. The typical prior art treatment technique for such multiple treatment point facilities is to deliver a large dose of chlorine to the piping inlet to the facility, thereby also delivering chlorine at the same time at, or above, the desired effective dosage levels to all of the numerous treatment points downstream of the piping inlet. Because of the loss of treatment effectiveness of chlorine over time, the dosage level of the chlorine at the inlet in single point treatment systems must be high enough that enough chlorine remains to be effective at the treatment point farthest removed from the inlet. However, this approach requires that large quantities of chlorine be provided at the inlet with resultant high capital cost and operating cost and exposes the piping system to high levels of highly reactive chlorine ions.

SUMMARY OF THE INVENTION

Among the several advantages of this invention is the selective (and, as may be desired, the sequential) target dosing of treatment additive into a facility utilizing water containing biological organisms for effectively treating the organisms throughout their residence time in the facility, without causing corrosion, chemical reaction or other detrimental action from the additive or environmental discharge problems. The treatment additive of the invention, as used for biofouling, comprises an oxidizing agent, such as chlorine ions or ozone, and a source of copper ions, both at relatively low dosage levels.

In accordance with this invention, a treatment additive may be delivered from a single source of additive to multiple points along the piping system of a facility to prevent biofouling at each location of the facility requiring treatment, but without copper ion buildup. In one embodiment of the invention doses of the treatment additive are delivered sequentially at the predetermined dosage level from the source of treatment additive and are targeted to the desired points along the piping system. This sequential target dosing of treatment additive significantly reduces the quantity of treatment additive required, as well as the number of treatment additive devices. Together, these reductions of additive and equipment significantly lower the capital costs and operating expenses for biofouling treatment of a facility.

As used in a desalinization plant, this invention provides for the delivery of relatively low dosage levels of oxidizing agent and even lower levels of copper ions into the piping system of the plant upstream of the reverse osmosis membrane. The dosage level of the oxidizing agent and copper ions is sufficient to inhibit growth of biological organisms that would otherwise grow on and thus adversely affect permeability of the filter media and/or membranes, but are low enough to avoid detrimental chemical reaction with the media. As used to protect water filters, this invention provides for the delivery of treatment additive upstream of the filters to prevent the growth of biological organisms on the membrane material. As used to reduce biofouling of a facility having heat rejection devices and heat transfer passaging for cooling water, this invention provides for the delivery of oxidizing agent at the inlet of the piping system of the facility, and oxidizing agent and copper ions upstream of the heat transfer passaging. As used to treat sea water or water produced from a well for downhole injection into a water-bearing formation of a hydrocarbon reservoir, this invention provides a source of oxidizing agent for delivering low dosages of such agent into the piping of the facility upstream of the filter equipment of the injection equipment and a source of copper ions for delivering even lower dosages of copper ions to the piping upstream of the filter. As used to treat a fire water system, this invention provides a source of oxidizing agent for delivery of oxidizing agent and a source of copper ions for delivery of copper ions, with both types of ions being delivered into the piping at the inlet to the fire water system to inhibit the growth of biological organisms in the system.

Other advantages and features will be, in part, apparent and, in part, pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENTS

Figure 1:
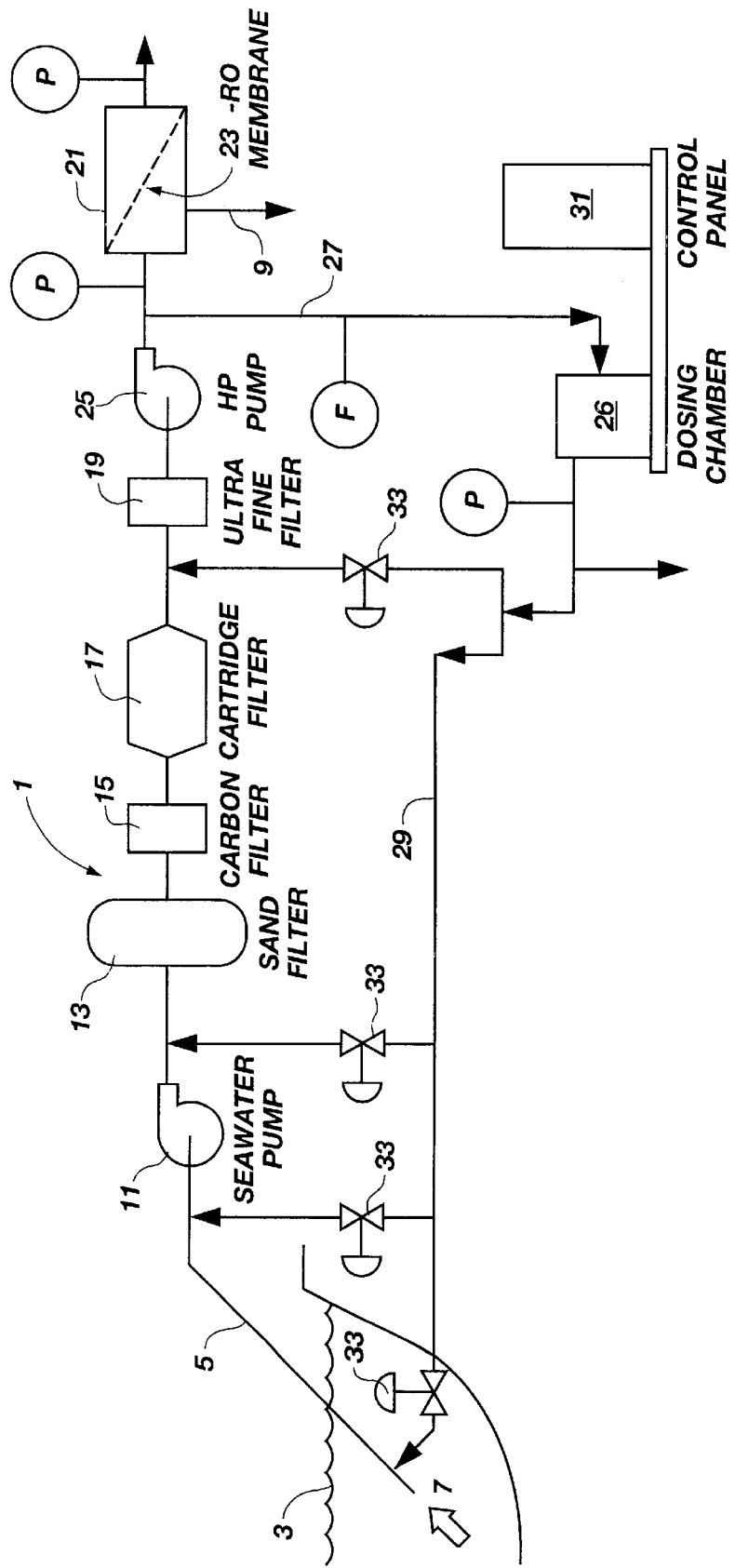
FIG. 1 is a flow diagram of a desalinization plant, showing the flow of water past the various filtration stations and the application of biofouling reduction treatment of this invention.

Referring to FIG. 1 of the drawings there, is generally indicated at 1 a desalinization plant for the treatment of raw water 3, such as sea water or brines, to remove undesirable organic and inorganic material, so as to make fresh or potable water. Such plants are often located in areas, such as the Mid-East, having little or no fresh water but easy access to sea water.

Desalination plant 1 comprises piping 5 extending from an inlet 7 in communication with a source of raw water to be treated to an outlet 9 discharging fresh water. A pump 11 is provided for lifting the raw water from the inlet and pressurizing the water in the piping 5 to move it to the outlet. At points along and in fluid communication with the piping is a series of filtration stations for removing the unwanted organic and inorganic materials. The desalinization plant includes one or more first coarse filters 13, such as a sand media bed filter, to remove relatively large particles suspended in the raw water. This is followed by one or more organic material removal filters 15, such as an activated carbon media bed filter, for removing oil and similar material. This is followed by one or more cartridge filters 17 and an ultrafiltration filter 19 for removing small suspended materials from the raw water. Final filtration is done at a reverse osmosis cell 21 utilizing a reverse osmosis membrane media 23 which blocks the flow of dissolved inorganic ions, such as $K^+$, $Cl^-$, $Na^+$, and $OH^-$, past the membrane while allowing the flow of fresh water through the membrane. A high pressure pump 26 creates sufficient water pressure at the upstream side of the membrane to overcome the osmotic pressure across the membrane media 23.

As described earlier, problems have arisen in the operation of prior desalinization plants (and, more particularly, in the operation of the membrane media of these plants) that significantly reduce their efficiency. The raw water to be treated not only contains undesirable organic and inorganic material and dissolved ions, but also biological microorganisms that tend to grow on the upstream face of the membrane medium, thereby adversely affecting the permeability of the medium and its filtration efficiency. The prior art approach for treating this biological growth is to provide a heavy dose of chlorine (e.g., a dosage level of 1–2 p.p.m) to the water upstream of the reverse osmosis cell. However, the material of construction of the reverse osmosis membrane media may chemically react with chlorine at these concentration levels and cause the very type of problem (i.e., the alteration in membrane permeability) that the chlorine, in part, was intended to overcome.

The biofouling reduction apparatus of this invention, as shown in FIG. 1, comprises a suitable source of treatment additive, such as dosing chamber 25, for introducing treatment additive at a predetermined dosage level into treatment water, a side stream 27 supplying water to the dosing chamber, flow connectors (collectively indicated at 29) extending between the dosing chamber and points along the raw water piping, a control panel or controller 31 for controlling the operation of the dosing chamber, and valves (collectively indicated at 33) positioned along the flow connectors to operate in a so-called sequential target dosing mode which delivers treatment additive of predetermined composition to selected points along the piping at predetermined times and in predetermined concentrations for enhanced efficiency and effectiveness of biofouling treatment.

The treatment additive comprises oxidizing agents, such as hydrogen peroxide, ozone or chlorine, and may include copper ions. The copper ions may be obtained from copper solutions, such as copper sulfate or copper citrate, or from an electrolytic cell. One acceptable cell design for producing both copper and chlorine ions is generally described and shown in U.S. Pat. No. 4,869,016, with this patent further describing the synergistic effects of these materials on biofouling treatment. In addition, U.S. Pat. No. 5,292,405 describes a so-called center-tap version of this type of electrolytic cell. It produces ions but does not produce an electrical charge on the water.

The controller 31 is a programmed logic controller (or PLC) which monitors and controls the dosage levels of the oxidizing agent and, as needed, the copper ions at the dosing chamber to yield treatment of the biological organisms at high levels of effectiveness and efficiency. A typical dosing level of oxidizing agent is 50 ppb or ug/l ($10^{-6}$ g/l) and of copper ions is 5 ug/l. The controller further monitors and controls the operation of the dosing chamber 25 and the valves 33 in the flow connectors 29 to deliver the treatment additive in a sequential target dosing mode, as well as for an operational duty cycle no longer than that required for effective treatment. In that regard, some biofouling treatment applications have been found to require the use of treatment additive for as little as two (2) hours per day.

In operation, the biofouling reduction apparatus receives the side stream of water 27, preferably taken downstream of at least one of the filters, introduces the treatment additive to the stream, and delivers the treatment additive carried in the water to the various points along the piping 5 where equipment requires biofouling treatment. In the desalinization plant of FIG. 1, the piping inlet 7 receives treatment additive comprising both oxidizing agent and copper ions to protect the inlet and piping extending to the pump 11. At the pump, treatment additive is again delivered but it need not comprise both oxidizing agent and copper ions. While the effectiveness of the oxidizing agent decreases with respect to time as the water flows along the piping and must be replenished for effective treatment, the copper ions generally do not dissipate and remain present and effective throughout the travel of the water through the piping to the reverse osmosis cell 21 where they are removed. In like manner, treatment agent, in the form of oxidizing agent, is delivered upstream of the sand filter 13, organic material removal filter 15, cartridge filter 17, ultrafiltration filter 19 and reverse osmosis cell 21. With the use of sequential target dosing, the concentration of the oxidizing agent, when it takes the form of chlorine ions, is so low that there is no chemical reaction with the reverse osmosis membrane media 23, and presents no environmental concern. The biofouling reduction apparatus and techniques of this invention maintain the reverse osmosis membrane media 23 free of biofouling and maintain operation at optimum permeability while utilizing small capacity equipment operating at low costs. A further benefit of this invention is the enhanced efficiency of the operation of the filters upstream of the reverse osmosis cell 21. The reverse osmosis membrane media 23 is also susceptible to biological growth and the treatment additive acts as a membrane protection aid for inhibiting biological growth on the media and maintaining filter performance.

Figure 2:
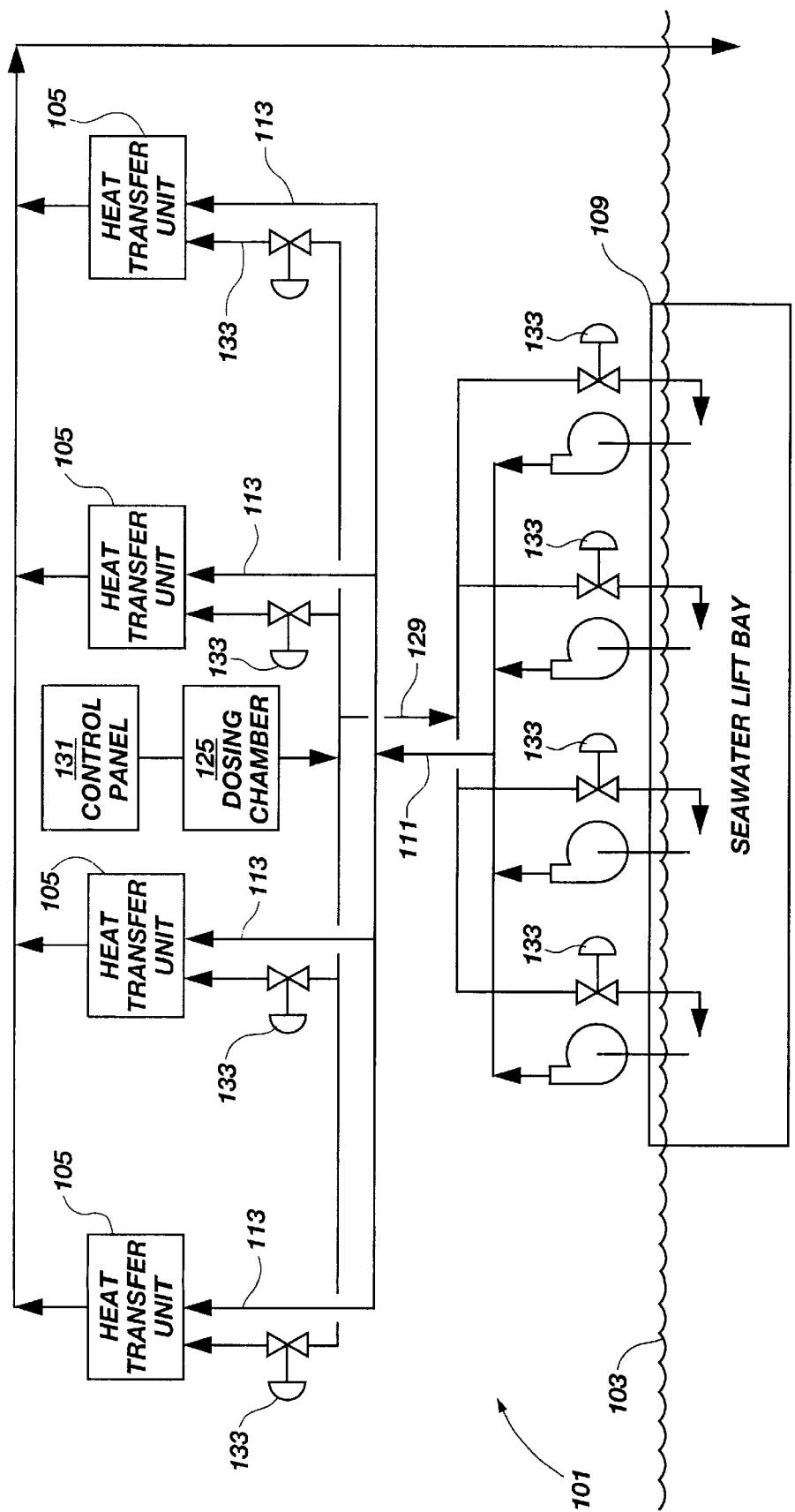
FIG. 2 is a flow diagram of a power plant located at a lake or ocean, showing the flow of cooling water past the various heat transfer units and the application of biofouling reduction treatment of this invention.

Referring now to FIG. 2, a plant, such as a power plant generally indicated at 101, is shown receiving cooling water from a source of raw water 103 from a source such as a lake or the ocean to cool heat generating devices at one or more suitable heat transfer units (collectively indicated at 105). The water is lifted by pumps (not shown) at a single or, as shown in FIG. 2, a multiple station sea water lift bay 109 (also referred to "cooling water inlets") and is moved via piping 111 to the passaging (collectively indicated at 113) of the heat transfer units. Often this water, whether it be fresh water or sea water, contains biological organisms which tend to attach themselves to the piping 111 and heat transfer passaging 113, thereby limiting the flow of water through the passaging and thus limiting the transfer of heat. As described earlier, the prior art approach for treating this biofouling problem was to continuously dose all of the cooling water with a dosage of chlorine high enough that a satisfactory treatment level of chlorine remained as the process water flowed past the heat transfer units. Because as much as 360,000 m$^3$/h of cooling water was treated with chlorine at a dosage of 3,000 ppb, large electrolytic cells capable of generating 1,000 kg per hour or more of chlorine was required.

In contrast, the biofouling reduction apparatus of power plant 101 of FIG. 2 comprises a relatively small dosing chamber 125, with an associated controller 131, and flow connectors (collectively indicated at 129) with remote control valves (collectively indicated at 133) extending between the dosing chamber and points along the piping. Treatment additive, provided at the dosing chamber, is delivered along the flow connectors 129 to the points along the piping requiring biofouling treatment. As shown in FIG. 2, the initial points of treatment are preferably at the cooling water inlets 109 and the other points of treatment are upstream of the heat transfer units 105. The controller 131 operates the dosing chamber 125 to deliver treatment additive comprising both oxidizing agent and copper ions to the cooling water inlets 109, and treatment additive comprising only oxidizing agent to the heat transfer units 105. The controller 131 operates the remotely controlled valves 133 so that the respective treatment additive is delivered at predetermined times and in predetermined quantities for the effective and efficient treatment of the biological organisms. For example, in using sequential target dosing, only the following doses of treatment agent are required: e.g., 750 ppb of oxidizing agent, and with or without 5 ppb of copper ions at each sequential dosing plant.

Figure 3:
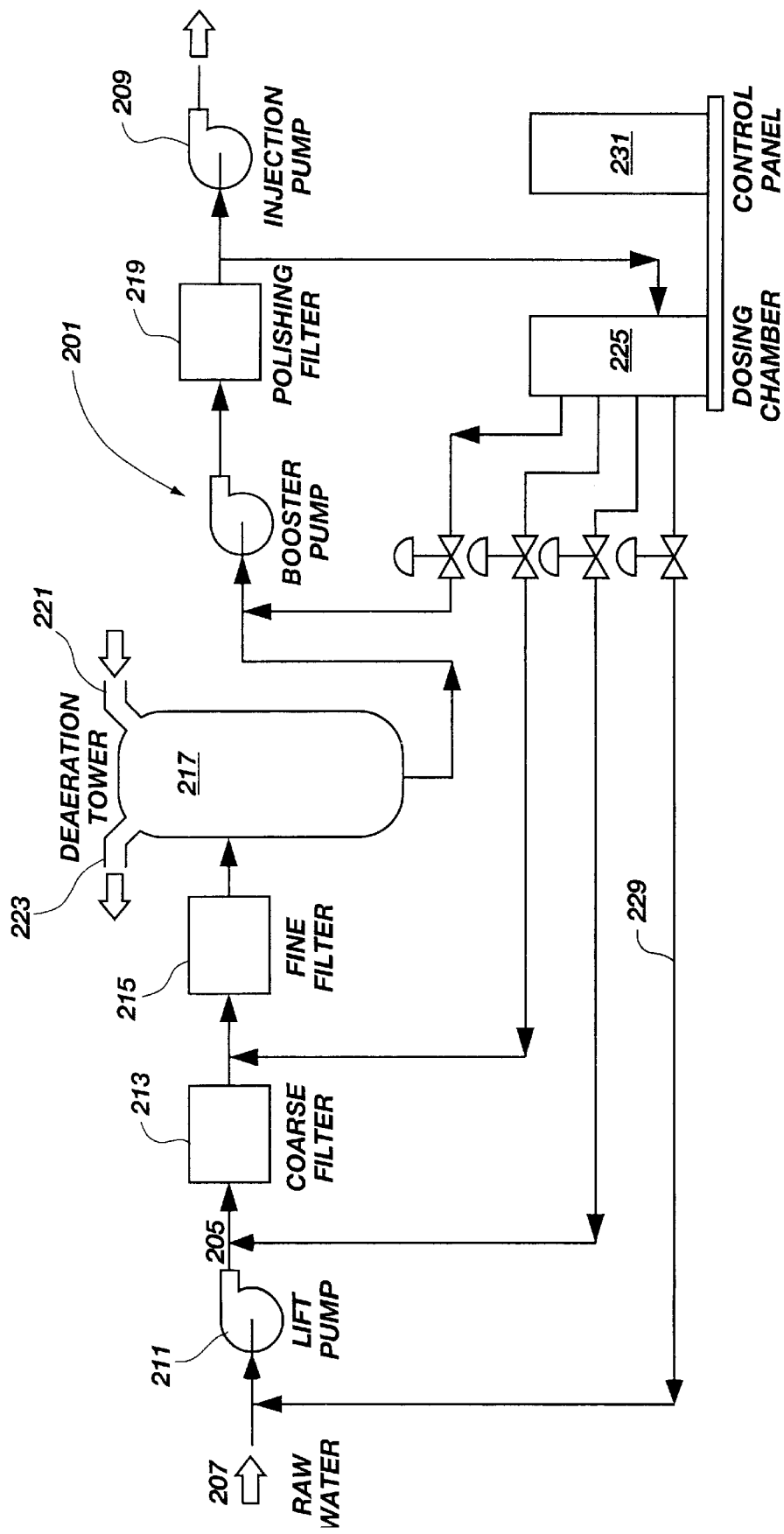
FIG. 3 is a flow diagram of an oilfield water injection facility, showing the flow of water past the various filtration stations and the application of biofouling reduction treatment of this invention.

Referring now to FIG. 3, an oilfield injection water treatment facility generally indicated at 201 is shown to comprise piping 206 extending from a raw water inlet 207 past various filters to a high pressure pump 209 for injection of the treated water downhole into a formation of a hydrocarbon reservoir. A lift pump 211 is provided at the raw water inlet 207 and moves the water via the piping 206 past one or more coarse filters 213, one or more fine filters 215, a de-aeration tower 217, a booster pump, a polishing filter 219 and finally to the injection pump 209. Chemical treatment equipment (not shown) typically is provided to inject chemicals, such as polyelectrolytes, coagulants, biocides, anti-foaming agents, oxygen scavengers and scale inhibitors, into the water to treat the water before injection. As with the earlier described desalinization plant 1 and power plant 101, the prior art approach to reducing biofouling in facilities of this type was to deliver a continuous large dose of chlorine to the raw water.

The biofouling treatment apparatus of this invention, as applied to the injection oilfield treatment facility 201, comprises a dosing chamber 225, controller 231 and flow connectors (collectively indicated at 229). The flow connectors 229 are shown positioned adjacent the dosing chamber 225 and it is contemplated they may be interior to or integral with that device. As described with the biofouling treatment apparatus described above for the desalinization plant 1 and power plant 101, the apparatus delivers treatment additive comprising oxidizing agent and copper ions at the raw water inlet 207 and treatment additive comprising only oxidizing agent upstream of the other treatment points. However, differing from the earlier-described facilities, the oilfield injection water treatment facility 201 of this invention makes synergistic use of the de-aeration tower 217. When an electrolytic cell is used in the dosing chamber 225 to generate chlorine ions for the treatment additive, the cell also generates hydrogen gas entrained and dissolved in the water. With prior art biofouling reduction systems, the quantities of chlorine and thus of resultant explosive hydrogen are so large that an additional associated hydrogen disengagement tank is required. However, with the apparatus of this invention, far smaller quantities of chlorine and hydrogen are generated and thus hydrogen disengagement can be accomplished at the de-aeration tank already present in the water injection circuit. As shown, this tank may be provided with inlet 221 for introducing air to flush the tank and a vent 223 for removing the air and released hydrogen.

Figure 4:
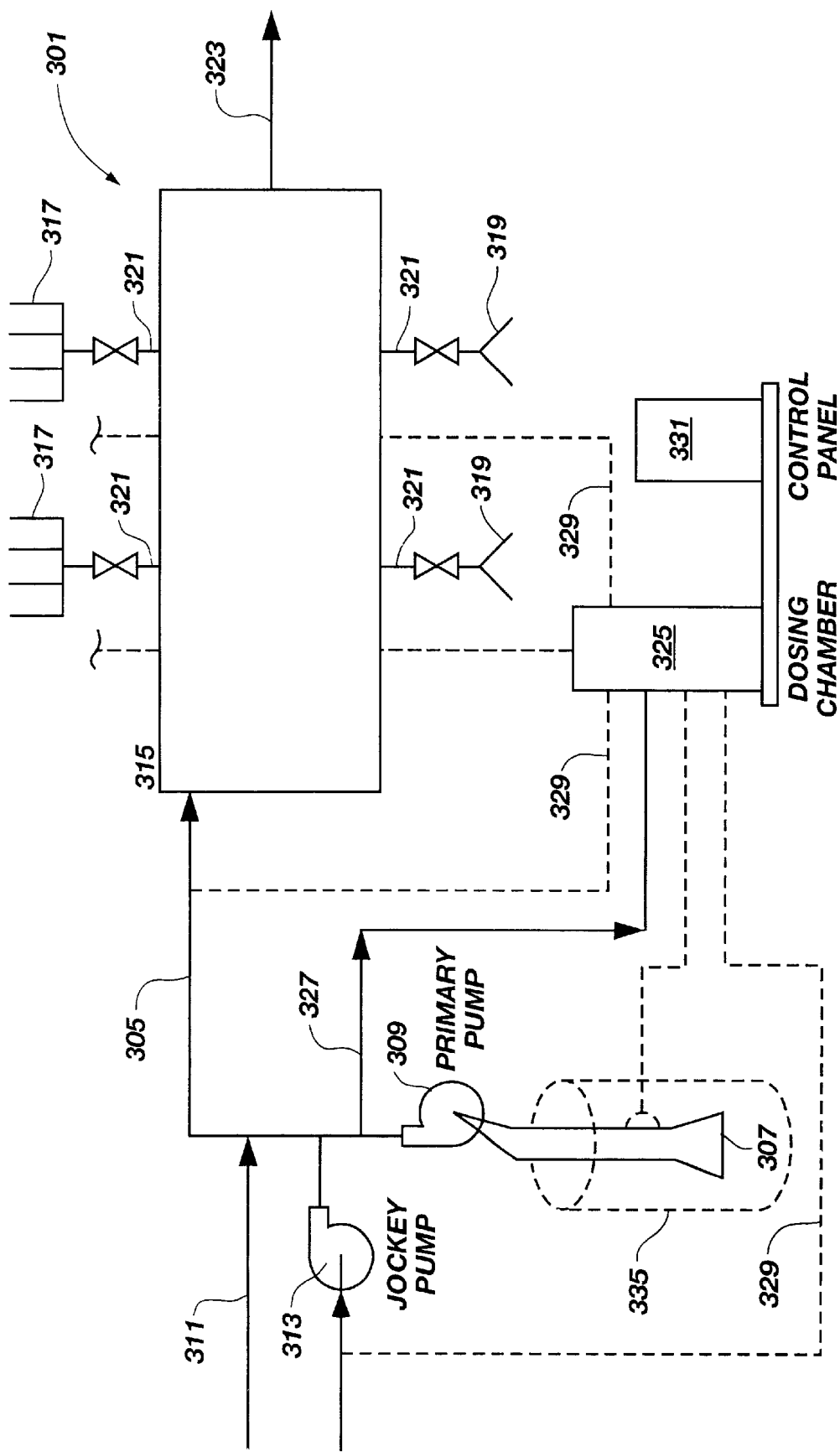
FIG. 4 is a flow diagram of a fire water system showing the flow of water to the sprinkler heads and deluge devices and the application of biofouling reduction treatment of this invention.

A marine fire water system is generally indicated at 301 in FIG. 4 for use in extinguishing fires by the discharge of water via sprinklers 317 or deluge systems 319 on board a ship, oilfield offshore rig or production and a storage facility (not shown). The system comprises piping 305, having an inlet 307 to raw water, such as sea water, carrying biological organisms. A high capacity main or primary pump 309 adjacent the inlet is available on a stand-by basis to be activated and operated when large quantities of sea water are required to extinguish a fire. The main pump is periodically operated on a test basis (e.g., one hour per week) to confirm the operability of the system. Otherwise, it is operated only in emergency.

However, it is necessary to keep the system charged with water under pressure, so that the system can respond immediately in extinguishing a fire, and thus operate during the start-up time of the main pump in an emergency. To do this, a secondary source of water under pressure is provided, either in the form of a side stream of water via pipe 311 from other pressured water (typically sea water) service, or a continuously operated, low capacity so-called jockey pump 313. The piping is in flow communication with a pipeline circuit 315 which includes the sprinklers 317 and deluge systems 319 connected via headers (collectively indicated as 321). The circuit further includes an outlet 323 for continuous discharge of water from the secondary source.

Several areas of potential biofouling arise in this system. A significant problem occurs at the raw water inlet 307 and the primary pump 309, which are continuously exposed to sea water and for which there is no movement of water at most times, thereby allowing the biological growth to readily attach to the piping 305. Another biofouling problem arises in the piping downstream of the secondary source of water and in the pipeline circuit 315, which is made more difficult by the low flow rate of water through these conduits. The biofouling reduction apparatus of this invention effectively addresses biofouling problems in these two areas. A third area presenting biofouling is in the headers 321. This problem is typically solved by draining the headers of water or flushing them with fresh water.

The biofouling reduction apparatus of this apparatus comprises a suitable source of treatment additive (such as dosing chamber 325), an associated controller 331, a side stream 327 of water to the dosing chamber 325, flow connectors (collectively indicated at 329) extending between the dosing chamber 325 and points along the piping 305 and pipeline circuit 315. The dosing chamber 325 includes valves (not shown) for controlling selective delivery of treatment additive along the flow connectors.

One of the flow connectors extends to the raw water inlet 307. To help contain the treatment additive at the raw water inlet 307, a generally cylindrical baffle or caisson 335 extends around the raw water inlet 307 and restricts the flow of water past the raw water inlet 307. Another of the flow connectors 329 extends to the piping downstream of the secondary source of water under pressure to protect the relatively large diameter piping 305. Further flow connectors are provided at points along the pipeline circuit 315.

In operation, the dosing chamber 325 and flow connectors 329 deliver treatment additive comprising both oxidizing agent and copper ions to the raw water inlet 307 and the point downstream of the secondary source of water. The dosing chamber and other flow connectors deliver treatment additive comprising only oxidizing agent to the points along the pipeline circuit. The controller 331 controls the operation of the dosing chamber and the associated valving to provide treatment additive of a predetermined composition at a predetermined dosage and for a predetermined time for sequential target dosing of the treatment additive. This technique is particularly effective for marine fire systems, in that there may be several pipeline circuits, one for each deck or floor of a ship or offshore rig, with each circuit having a number of treatment addition points.

While a number of specific facilities have been described; namely, a desalinization plant 1, a power plant 101, an oilfield injection water treatment injection facility 201 and marine fire water system 301, the biofouling reduction apparatus and method of this invention could be used in any facility utilizing water carrying biological organisms tending to grow within these facilities and adversely affecting operation. Indeed, this apparatus and method are usable with any liquid, not just water, carrying biological organisms requiring treatment and any facility having one or more pieces of equipment, such as sulfate removal or ultrafiltration membranes, requiring protection.

In view of the above, it will be seen that the several advantages of the invention are achieved and the other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A desalinization plant utilizing reverse osmosis membrane media, the permeability of which is adversely affected by the growth of biological organisms on an upstream surface of the reverse osmosis membrane media and which further may be susceptible to adverse effects on permeability caused by chemical reaction with chlorine at levels sufficient to render the biological organisms inactive, the desalinization plant comprising:

piping having an inlet to water carrying inorganic material and biological organisms;

a pump moving water along the piping;

at least one filter along the piping for removing at least some particulate matter from the water;

a reverse osmosis cell along the piping downstream of the at least one filter having membrane media for removing inorganic ions from the water;

a source of oxidizing agent;

a conduit arrangement for delivering a first dosage of the oxidizing agent from the source of oxidizing agent into the piping upstream of the at least one filter and a second dosage of the oxidizing agent upstream of the reverse osmosis cell with the dosage levels of the oxidizing agent being well below that required to inhibit the growth of biological organisms when acting by itself; and a source of copper ions for delivering copper ions into the piping solely upstream of the at least one filter with a dosage level of the copper ions being below that of the oxidizing agent and below that required, when acting on their own, to inhibit growth of biological organisms but sufficient, when acting together with the oxidizing agent to effectively inhibit growth of biological organisms in the at least one filter and on the membrane media, whereby adverse changes in the permeability of the membrane media by growth of biological organisms and detrimental chemical reaction of the membrane media with the oxidizing agent are prevented and an amount of copper ion discharge from the desalinization plant is limited.

2. The desalinization plant of claim 1 wherein the source of copper ions delivers doses of copper ions at approximately a dosage level of five (5) parts per billion ($\mu$g/l) and the source of oxidizing agent delivers doses of oxidizing agent at approximately a dosage level of fifty (50) parts per billion ($\mu$g/l).

3. The desalinization plant of claim 1 wherein the source of oxidizing agent is an electrolytic cell for generating chlorine ions.

4. A method of desalinization of water carrying inorganic material and biological organisms in a reverse osmosis cell having membrane media, the permeability of which is adversely affected by the growth of biological organisms on an upstream surface of the membrane media and which further may be susceptible to adverse effects on permeability by chemical reaction with chlorine at levels sufficient to render the biological organisms inactive, the method comprising:

pumping water carrying inorganic material and biological organisms in piping to a reverse osmosis cell having membrane media, the pumping being conducted at a pressure sufficient to overcome the osmotic pressure of the membrane media;

filtering the water at a filter upstream of the reverse osmosis cell to remove at least some particulate matter in the water;

removing inorganic material from the water by passing the water through the membrane media;

delivering a first dose of oxidizing agent to the water upstream of the filter and a second dose of the oxidizing agent upstream of the reverse osmosis cell with produced ions being at a dosage level below that required to inhibit the growth of biological organisms when acting on its own; and delivering doses of copper ions solely upstream of the filter at dosage levels lower than the oxidizing agent dosage level and below that required, when acting on their own, to inhibit growth of biological organisms but sufficient, when acting together with the oxidizing agent to inhibit growth of microorganisms on the membrane media, whereby adverse effects on the permeability of the membrane media by biological growth and chemical reaction between the oxidizing agent and the membrane media are prevented and an amount of copper ion discharge downstream of the reverse osmosis cell is limited.

5. The method of claim 4 further comprising delivering copper ions at approximately a dosage level of five (5) parts per billion and the oxidizing agent at approximately a dosage level of fifty (50) parts per billion.

6. A filter system for filtering liquid containing particulate matter, inorganic ions and undesired biological organisms, the filter system employing media including at least one media, the permeability of which is adversely affected by growth of biological organisms thereon, the filter system comprising:

a plurality of filter units containing filter media and positioned in a serial flow arrangement;

piping for delivering the liquid containing particulate matter and biological organisms to the filter units at an upstream end of the serial flow arrangement;

a source of oxidizing agent;

a conduit arrangement configured for delivering doses of oxidizing agent into the piping upstream of at least two of the filter units of the plurality of filter units; and a source of copper ions for delivering doses of copper ions solely upstream of a first filter unit of said plurality of filter units at a dosage level lower than a dosage level of the oxidizing agent and sufficient, when acting together with the oxidizing agent, to inhibit the growth of biological organisms on the surface of the at least one media of the filter system.

7. The filter system of claim 6 wherein the source of copper ions delivers copper ions at approximately a dosage level of five (5) $\mu$g/l and the source of oxidizing agent delivers oxidizing agent at approximately a dosage level of fifty (50) $\mu$g/l.

8. A method of filtering liquid containing particulate matter and biological organisms using media susceptible to reduced permeability by growth of biological organisms thereon, the method comprising:

delivering the liquid containing particulate matter and biological organisms to an upstream end of a plurality of filter units positioned in a serial flow arrangement, at least one of the plurality of filter units employing the media;

delivering doses of oxidizing agent to the liquid upstream of at least two of the filter units of the plurality of filter units; and delivering doses of copper ions to the liquid solely upstream of a first filter unit of the plurality of filter units at a dosage level below a dosage level of the oxidizing agent and sufficient, when acting together with the oxidizing agent to inhibit the growth of biological organisms on the surface of the media and to enhance the filtration performance of the media.

9. A facility having a plurality of heat generating devices, each cooled by liquid flowing through heat transfer passages in heat transfer communication with each of the heat generating devices, with the liquid bearing biological organisms exhibiting a tendency to attach themselves to the heat transfer passages and reduce heat transfer and water flow through the heat transfer passages, the facility comprising:

piping having at least one inlet for receiving liquid and a plurality of outlets for delivering the liquid to the heat transfer passages associated with each of a plurality of heat generating devices positioned in a parallel flow arrangement;

at least one pump for conveying the liquid through the piping;

a source of oxidizing agent;

a conduit arrangement for delivering doses of oxidizing agent to the liquid proximate the at least one inlet of the piping and proximate the plurality of outlets of the piping upstream of at least two heat generating devices of the plurality of heat generating devices; and a source of copper ions delivering doses of copper ions to the liquid solely adjacent the at least one inlet of the piping at a dosage level below a dosage level of the oxidizing agent and sufficient, when acting together with the oxidizing agent to inhibit the growth of biological organisms in the piping and the heat transfer passages.

10. The processing facility as set forth in claim 9, further comprising a single source of oxidizing agent, a single source of copper ions and a flow connector configured for delivery of the oxidizing agent to multiple points along the piping.

11. A water treatment facility for treating water to be injected downhole into a water-bearing formation of a hydrocarbon reservoir by removing particulate matter and dissolved gases from the water before injection, the water treatment facility comprising:

at least one filter unit containing filter media susceptible to reduction in permeability by growth of biological organisms thereon;

piping having at least one inlet for receiving water carrying particulate matter and biological organisms;

a transfer pump moving water received through the at least one inlet along the piping to the at least one filter unit;

an injection pump downstream of the at least one filter unit for injecting the filtered water downhole into the water-bearing formation of the hydrocarbon reservoir;

a source of oxidizing agent;

a flow connector arrangement for delivering doses of oxidizing agent from the source of oxidizing agent into the piping at a plurality of locations along the piping, at least one location of the plurality of locations being adjacent the at least one inlet; and a source of copper ions for delivering doses of copper ions solely at a location upstream of the at least one filter unit at a dosage level lower than a dosage level of the oxidizing agent and sufficient, when acting together with the oxidizing agent to inhibit the growth of biological organisms in the at least one filter unit and to enhance filtration performance of the filter media.

12. The water treatment facility of claim 11 further comprising a de-aeration apparatus downstream of the at least one filter unit for removing gas entrained and dissolved in the water, with the de-aeration apparatus configured for removing any hydrogen gas generated at the source of copper ions.

13. The water treatment facility of claim 11 wherein the flow connector arrangement is configured to deliver doses of oxidizing agent to the piping upstream of the transfer pump and other doses of oxidizing agent upstream of the injection pump.

14. A fire water system for discharge of water carrying biological organisms and particulate matter tending to foul the fire water system when activated in response to a fire, comprising;

piping having at least one inlet to a source of water carrying biological organisms;

a main pump for conveying the water from the source through the piping;

a pipeline circuit in fluid flow communication with the piping and having a plurality of discharge valves for selective discharge of water under pressure and an outlet for continuous discharge of water from the pipeline circuit at a relatively low volume flow rate which is substantially less than the flow rate capacity of the pipeline circuit when the plurality of discharge valves are open;

a secondary source of water under pressure in flow communication with the piping and the pipeline circuit for delivery of water to be continuously discharged through the outlet for keeping the pipeline circuit charged with water under pressure;

a source of oxidizing agent;

a flow connector arrangement for delivering doses of oxidizing agent to the piping and at a plurality of locations along the pipeline circuit, at least one of said plurality of locations being adjacent the inlet; and a source of copper ions for delivering doses of copper ions to the piping solely adjacent the at least one inlet, the copper ions and the oxidizing agent being operative in combination to inhibit growth of the biological organisms in the piping and the pipeline circuit.

15. The fire water system of claim 14 wherein the flow connector arrangement is configured to deliver oxidizing agent to the piping adjacent the main pump and adjacent the secondary source of water under pressure.

16. The fire water system of claim 14 further comprising a baffle adjacent the at least one piping inlet for forming a zone of restricted flow of water at the inlet, with the flow connector arrangement configured to deliver oxidizing agent from the source of oxidizing agent and copper ions from the source of copper ions to the zone of restricted flow.

17. A liquid piping circuit for circulating liquid containing biological organisms tending to foul the circuit and an end use device along the liquid piping circuit utilizing the liquid, the liquid piping circuit comprising:

piping having at least one inlet to a source of liquid carrying biological organisms;

a pump for conveying the liquid along the piping;

at least one end use device connected to the piping for utilizing the liquid;

a source of treatment additive for inhibiting growth of biological organisms;

a flow connector arrangement extending between the source of treatment additive and at least first and second points along the piping for delivery of the treatment additive thereto, the first point of the at least first and second points being adjacent the at least one inlet and the second point of the at least first and second points being upstream of the at least one end use device; and a controller for initiating selective and sequential delivery of doses of treatment additive through the flow connector arrangement from the source of treatment additive to the piping at the first point and of treatment additive to the piping at the second point.

18. The liquid piping circuit of claim 17 wherein the at least one end use device comprises a plurality of end use devices, with the controller programmed for providing selective and sequential delivery of treatment additive from the source of treatment additive to said first point, and then to the piping upstream of each of the plurality of end use devices.

19. A method of preventing biofouling in a liquid piping circuit circulating liquid containing biological organisms tending to foul the circuit with at least one end use device in the liquid piping circuit utilizing the liquid, the method comprising:

providing piping having at least one inlet to a source of liquid carrying biological organisms and in communication with at least one end use device for utilizing the liquid;

continuously flowing the liquid through the piping;

providing a source of treatment additive for inhibiting growth of the biological organisms in the liquid and a flow arrangement extending between the source of treatment additive and multiple points along the piping; and delivering treatment additive via the flow connector arrangement from the source to at least two points of the multiple points along the piping, a first point of the at least two points being adjacent the at least one inlet and a second point of the at least two points being upstream of the at least one end use device, wherein the delivery of treatment additive is done selectively and sequentially from the source of treatment additive in doses to said first point along the piping and then in doses to said second point along the piping.

20. A liquid piping circuit for flow of liquid requiring treatment by a treatment additive which has a treatment effectiveness which decreases with time as the liquid flows along the liquid piping circuit to at least one end use device along the liquid piping circuit utilizing the liquid, the liquid piping circuit comprising:

piping having at least one inlet to a source of liquid requiring treatment by a treatment additive;

a pump for conveying the liquid along the piping;

at least one end use device adapted to utilize the liquid connected to the piping;

a source of treatment additive subject to losing treatment effectiveness with the passage of time, delivering the treatment additive to at least two points along the piping, a first point of the at least two points being adjacent the at least one inlet and a second point of the at least two points being upstream of the at least one end use device;

a flow connector arrangement extending between the source of treatment additive and the at least two points along the piping, a first point of the at least two points being adjacent the at least one inlet and a second point of the at least two points being upstream of the at least one end use device, for delivering doses of the treatment additive to the at least two points.

21. A method of treating liquid in a liquid piping circuit with a treatment additive which has a treatment effectiveness which decreases with time as the liquid flows along the liquid piping circuit, the liquid piping circuit including at least one end use device utilizing the liquid, the method comprising:

providing liquid piping having at least one inlet to a source of liquid to be treated by a treatment additive which has a treatment effectiveness which decreases with time, and the at least one end use device adapted to utilize the liquid;

delivering the treatment additive from a single source thereof in doses to at least two points along the piping, a first point of the at least two points being adjacent the at least one inlet and a second point of the at least two points being adjacent the at least one end use device; and selectively and sequentially delivering doses of the treatment additive to the first point along the piping and then to the second point.

22. A process liquid treatment mechanism for treating liquid flowing in a liquid piping circuit having an inlet to a source of liquid requiring treatment and a plurality of end use devices connected to the liquid piping circuit utilizing the liquid, the mechanism comprising:

a dosage delivery mechanism for receiving treatment additive from a source thereof;

a plurality of flow connectors extending between the dosage delivery mechanism and a respective plurality of points along the liquid piping circuit;

the dosage delivering mechanism including valving for selectively and sequentially directing a predetermined dosage of the treatment additive from the source thereof to at least one predetermined flow connector of the plurality for a predetermined period of time, and a delivery device for flowing the treatment additive along the at least one predetermined flow connector under pressure to a respective point along the liquid piping circuit; and a controller configured for controlling the operation of the valving to selectively and sequentially deliver the predetermined dosage.

23. The process liquid treatment mechanism of claim 22 further comprising a controller for controlling the operation of the valving to selectively and sequentially deliver the predetermined dosage.

* * * * *

UNITED STATES PATENT AND TRADEMARK OFFICE
CERTIFICATE OF CORRECTION

PATENT NO. : 6,183,646 B1  
DATED : February 6, 2001  
INVENTOR(S) : Edward Emyr Williams et al.

It is certified that error appears in the above-identified patent and that said Letters Patent is hereby corrected as shown below:

Column 1,  
Line 6, delete the comma after "reduction"

Column 3,  
Line 27, insert a comma after "invention"

Column 4,  
Line 28, insert a comma after "drawings" and delete the comma after "there"  
Line 55, change "26" to -- 25 --

Column 5,  
Lines 10 and 43, change "25" to -- 26 --

Column 6,  
Line 67, change "206" to -- 205 --

Column 7,  
Line 1, after "pressure" and before "pump" insert -- injection --  
Line 4, change "206" to -- 205 --  
Line 12, insert a hyphen between "earlier" and "described"  
Line 17, change "injection oilfield" to -- oilfield injection water --

Signed and Sealed this

Sixteenth Day of March, 2004

JON W. DUDAS  
*Acting Director of the United States Patent and Trademark Office*